United States Patent [19]

Heil, Jr. et al.

[11] Patent Number: 5,016,808
[45] Date of Patent: May 21, 1991

[54] IMPLANTABLE TAPERED SPIRAL ENDOCARDIAL LEAD FOR USE IN INTERNAL DEFIBRILLATION

[75] Inventors: Ronald W. Heil, Jr., Roseville; Robert C. Owens, Forest Lake, both of Minn.

[73] Assignee: Cardiac Pacemakers, Inc., St. Paul, Minn.

[21] Appl. No.: 461,980

[22] Filed: Jan. 8, 1990

Related U.S. Application Data

[62] Division of Ser. No. 407,052, Sep. 14, 1989.

[51] Int. Cl.⁵ .............................................. A61N 1/00
[52] U.S. Cl. .................................... 228/176; 264/173; 128/785
[58] Field of Search ........................ 228/176; 29/592.1; 425/393; 264/173

[56] References Cited

U.S. PATENT DOCUMENTS

| | | | |
|---|---|---|---|
| 3,760,812 | 9/1973 | Timm et al. | 128/784 |
| 4,551,292 | 11/1985 | Fletcher et al. | 425/393 |
| 4,573,481 | 3/1986 | Bullara | 128/784 |
| 4,764,324 | 8/1988 | Burnham | 264/209.4 |
| 4,860,769 | 8/1989 | Fogarty et al. | 128/786 |

*Primary Examiner*—Kenneth J. Ramsey
*Attorney, Agent, or Firm*—Haugen and Nikolai

[57] ABSTRACT

An improved electrocardial lead for use with an automatic implantable cardioverter/defibrillator (AICD) comprises an elongated, flexible, plastic tubular catheter body which is preformed so that when unconstrained, it assumes the shape of a tapered spiral or helix. The catheter body supports a defibrillating electrode attached to the exterior wall of the catheter body and is connected by a suitable cable to a proximal connector for mating with the AICD pulse generator. The improved lead also includes a tip electrode for sensing cardiac activity and providing information to the AICD pulse generator for controlling its operation. The lead of the present invention is intended for endocardial emplacement with the electrode structures predominantly in the right ventricle and provides substantially increased electrode surface area in contact with heart tissue as compared to prior art endocardial defibrillating leads and, thus, maximizing the energy delivered to the heart during defibrillation.

5 Claims, 2 Drawing Sheets

5,016,808

IMPLANTABLE TAPERED SPIRAL ENDOCARDIAL LEAD FOR USE IN INTERNAL DEFIBRILLATION

This is a divisional of application Ser. No. 07/407,052, filed Sept. 14, 1989.

BACKGROUND OF THE INVENTION

I. Field of the Invention

This invention relates generally to a novel electrode arrangement for use with an automatic implantable cardioverter/defibrillator (AICD), and more particularly to the design of a highly flexible endocardial lead adapted for placement predominantly in the right ventricle and possessing a shape characteristic and electrode placement for maximizing the energy deliverable to heart tissue during a defibrillation episode.

II. Discussion of the Prior Art

A good synopsis of the prior art relating to electrode arrangements for use with AICD devices is set forth in the section "BACKGROUND OF THE INVENTION" of U.S. Pat. No. 4,662,377 to Heilman et al, which is hereby incorporated by reference. That patent goes on to describe a defibrillating lead in the form of an elongated catheter having a distal tip electrode and with a distal defibrillating electrode insulated therefrom and spaced a short distance proximally thereof. Each of these two electrodes is intended for placement in the right ventricle with the tip electrode disposed in the right apex thereof. A third and more proximal electrode is located at a position which will be within the superior vena cava when the distal tip is at the right ventricular apex. The endocardial lead described in the aforereferenced Heilman et al Patent is intended to cooperate with a flexible patch electrode which is electrically connected to the proximal electrode disposed in the superior vena cava, but the patch itself is positioned between the skin and the rib cage proximate to the left ventricular apex of the heart. When the AICD pulse generator detects a life-threatening, abnormal heart rhythm, it will issue a cardioverting or defibrillating pulse across the distal electrode and the combination of the proximal electrode and the patch electrode.

While the device of the aforereferenced Heilman et al patent affords the advantage of being substantially less traumatic in its placement than systems requiring a thoracotomy, the amount of electrode surface in contact with heart tissue within the right ventricle is necessarily limited. The electrode itself comprised a spring-like arrangement of closely wound turns, e.g., 20 turns per inch, which necessarily adds stiffness or rigidity to the portion of the catheter supporting the electrode surface. As such, it becomes difficult for the electrode area to conform to the interior of the heart and to move in conjunction with the natural contractions of the heart.

OBJECTS

It is accordingly a principal object of the present invention to provide an improved endocardial lead structure for use with an AICD device.

Another object of the invention is to provide an endocardial lead for use with an AICD device which has increased electrode surface contained within the right ventricle of the heart.

Still another object of the invention is to provide an endocardial lead for use with an AICD which, while increasing the amount of electrode surface engaging the heart tissue within the right ventricle, still remains highly flexible and non-injurious to endocardial tissue.

SUMMARY OF THE INVENTION

The foregoing features and advantages of the invention are achieved by providing an elongated, flexible plastic tubular catheter body which, when unconstrained, will assume a spiral shape with the coils thereof being of decreasing radius from a predetermined proximal location to the distal end. Formed on the distal tip is a sensing and pacing electrode. A conductor connected to the tip electrode extends through the catheter body to a proximal end connector pin. Affixed to the outer surface of the catheter body is a defibrillation electrode in the form of a ribbon which is wound in candy-stripe fashion over that distal portion of the catheter body which would find itself in the right ventricular chamber during use. The proximal end of the ribbon electrode is coupled by a conductor which passes through the catheter body to the proximal connector. The spiral electrode of the present invention would be used in combination with a subcutaneous or myocardial patch electrode which acts as a return electrode.

The spiral electrode of the present invention is installed by first inserting a stylet through the lumen of the catheter body or through a coil located within the lumen to effectively straighten out the convolutions of the lead. It would then be routed through the vascular system until the distal tip electrode is located at the right ventricular apex. Now, when the stylet is removed, the memory property of the plastic body or other shape determining means will result in its reassuming its tapered spiral shape and the helically-wound defibrillation electrode will engage an increased amount of cardiac tissue within the right ventricle, at least as compared to prior art AICD lead systems.

DESCRIPTION OF THE DRAWINGS

The foregoing features and advantages of the invention will be better understood from the following detailed description of the preferred embodiment, especially when considered in conjunction with the accompanying drawings in which like numerals in the several views refer to corresponding parts.

DESCRIPTION OF THE PREFERRED EMBODIMENT

Figure 1:
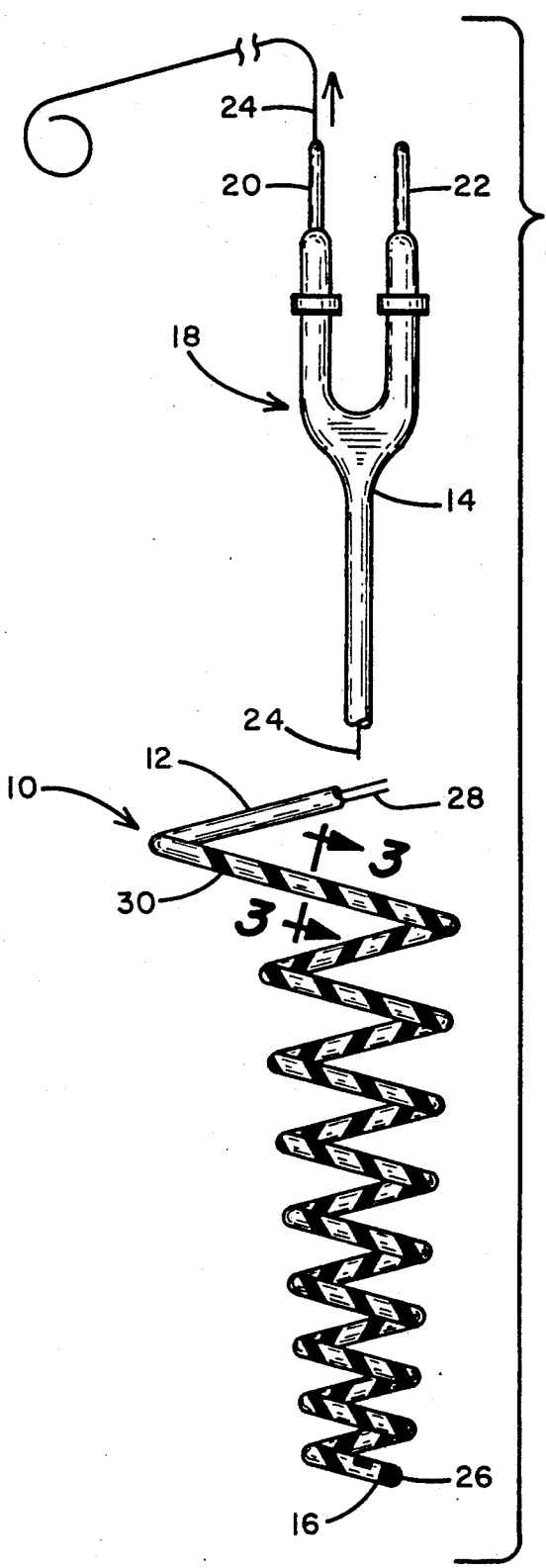
FIG. 1 is an enlarged, perspective view of the AICD endocardial lead comprising a preferred embodiment of the invention.

Referring to FIG. 1, there is shown a perspective view of the implantable tapered spiral endocardial lead for use with an automatic implantable cardioverter/defibrillator. It is indicated generally by numeral 10 and includes an elongated, flexible plastic tubular member 12 which is preferably formed from polyurethane, silicone rubber or any other biocompatible, medical grade material commonly used in the fabrication of endocardial leads used with cardiac pacer pulse generating equipment. The tube 12 has a proximal end 14 and a distal end 16 and at least one lumen 13 extending substantially the entire length thereof. Affixed to the proximal end 14 of the flexible plastic tubular member 12 is a proximal connector 18 having bifurcated terminals 20 and 22 adapted to mate with appropriate connector receptacles on the AICD pulse generator (not shown). The connector pin 20 has a concentric, longitudinal bore formed therethrough for receiving a stylet 24 which can then be passed through the lumen of the tubular body 12, all as will be more particularly described hereinbelow.

During manufacture of a polyurethane device, a predetermined portion at the distal end of the tubular body is threaded onto a spiral mandrel and then the tube is subjected to an elevated temperature below the melting point but above the softening point. Then, when subsequently cooled, removed from the mandrel and suspended as in FIG. 1, it takes on a spiral shape when it is otherwise unconstrained. Materials such as a silicone rubber would require steps taken during extrusion or molding to accomplish the same shape configuration.

Affixed to the distal end 16 of the tubular body 12 is a tip electrode 26 used for pacing and sensing electrical activity, typically ventricular depolarization signals. A conductor 28 threads through the lumen of the tubular body 12 to make electrical contact with one or the other of the terminal pins 20 or 22.

With continued reference to FIG. 1, spirally wound in candy-stripe fashion on the distal portion of the catheter is a conductive ribbon 30 which may preferably comprise a flexible strip of titanium, titanium alloy, platinum or platinum iridium alloy appropriately bonded to the exterior surface of the catheter body by a medical grade adhesive or other means. It has been found appropriate to employ a double-folded screen of the metallic electrode material in forming the ribbon, the doublefolding eliminating any frayed wire edges. Alternately, electrode 30 may comprise a fine, flexible metallic braid surrounding the catheter like a sock. The screen may be bonded to the tubular body 12 by a dilute solution of uncured polymer in an appropriate volatile solvent. Once the solvent carrier evaporates and coating cures, the electrode screen material becomes securely attached to the lead body.

Figure 2:
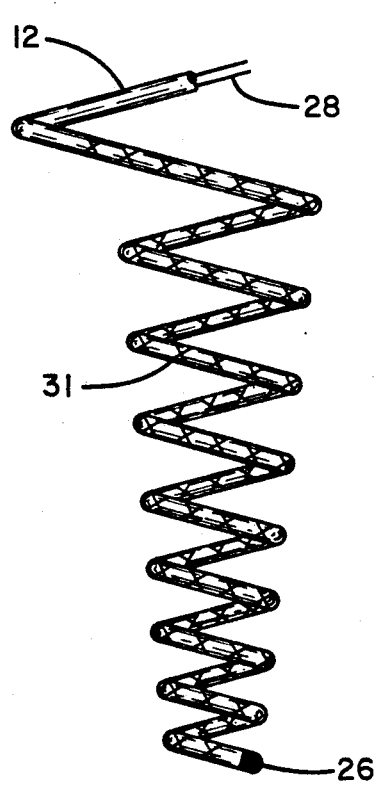
FIG. 2 is a fragmentary view of an alternative electrode configuration.

With reference to FIG. 2, a different defibrillator electrode attached to the distal portion of the catheter may comprise a conductive deposited electrode 31. Such a deposited electrode may be formed by, e.g., plating or vapor deposition a conductive material onto the tubular body. The deposited electrode on the tubular body provides excellent flexibility properties and does not materially add to the overall stiffness of the lead assembly. In the preferred embodiment, a drawn, braised and stranded (DBS) conductor extends from the second terminal pin 22, through the lumen and the wall of the tube 12 to connect to the proximal end of the surface electrode 30.

Figure 3:
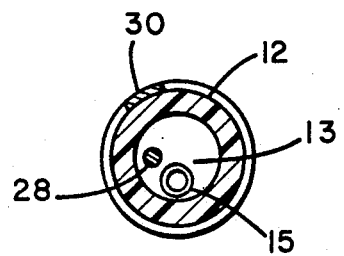
FIG. 3 is a cross-sectional view taken along the lines 3—3 in FIG. 1.

FIG. 3 shows a cross-section of the lead of the present invention taken along the lines 3—3 in FIG. 1. The silicone rubber or polyurethane tubular member 12 defines at least one lumen 13 which extends from the proximal end 14 thereof all the way to the distal tip electrode 26. The conductor 28 passes the length of the lumen 13 to electrically join the proximal terminal 22 to the distal electrode 26. The lumen 13 also provides a channel through which the stylet 24 may pass, the stylet being sufficiently rigid to straighten out the convolutions of the spiral portion of the lead when fully inserted, yet sufficiently flexible to permit the intravascular insertion of the catheter into the right ventricle. An optional coil 15 may be employed in lumen 13 to serve as a guide for the stylet.

Figure 4:
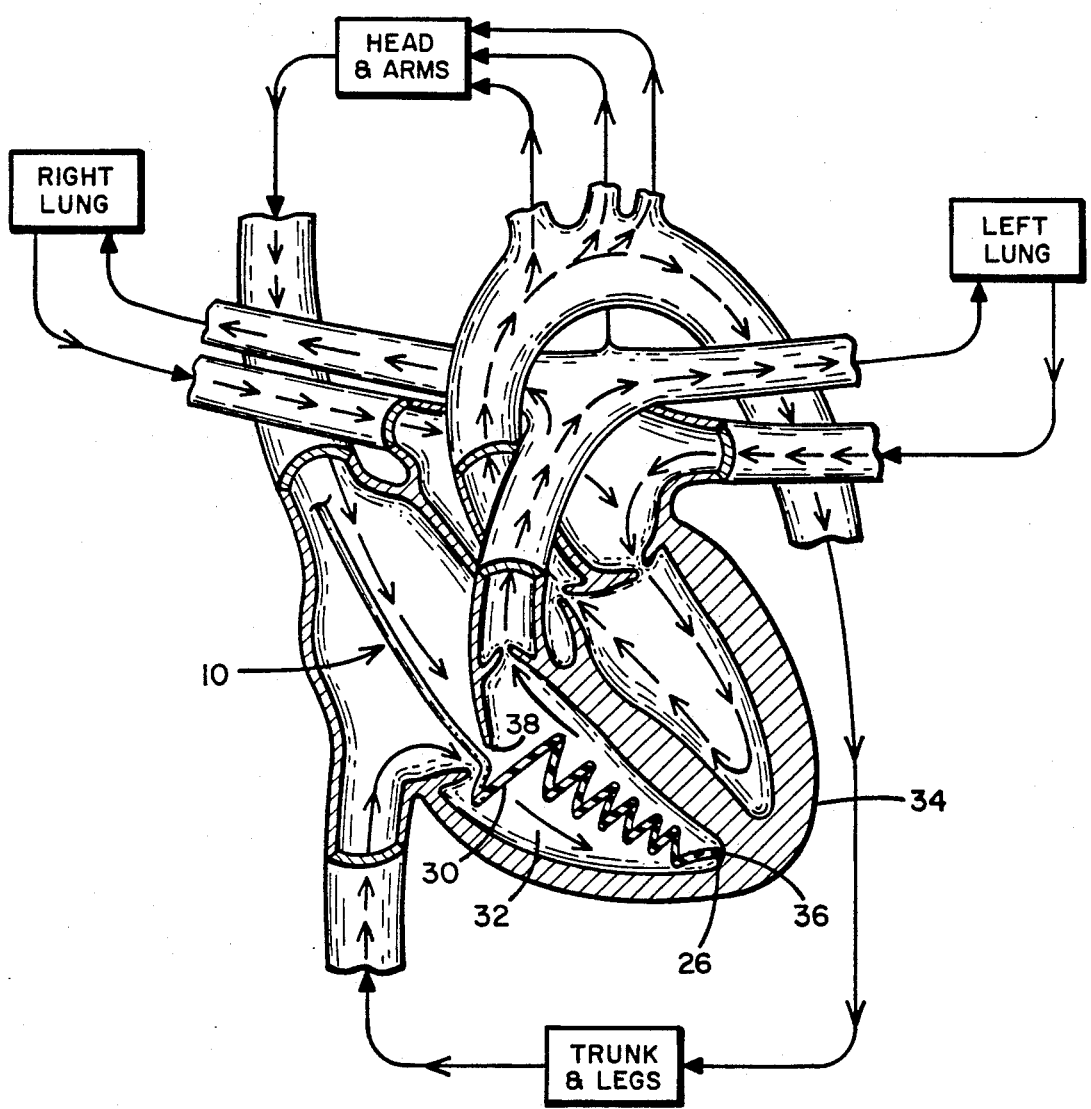
FIG. 4 shows the lead of FIG. 1 installed in the right ventricle of a heart.

Referring next to FIG. 4, the endocardial defibrillation lead 10 is shown as being installed in the right ventricle 32 of the heart 34. The distal tip electrode 26 is disposed in the right ventricular apex 36 and the stylet 24 has been removed allowing the distal end portion of the lead 10 to assume its tapered spiral shape. The exterior electrode engages the tissue structures including the endocardium and the trabeculae at multiple locations, thereby effectively increasing the area through which the defibrillating energy is distributed. It can be seen that when the lead is properly positioned as in FIG. 4, the spiral portion of the lead runs predominantly below the tricuspid valve 38 to the apex 36 of the right ventricle where the sensing/pacing electrode 26 is positioned.

It is also contemplated that some type of positive fixation technique, such as flexible tines, endocardial screws, barbs, etc., may be located at the distal end of the catheter as is the case with many standard cardiac pacing electrodes.

Rather than preforming the tubing on a spiral mandrel and appropriately heating the material above the softening point of the plastic or otherwise extruding or molding the part, it is also possible to impart the desired spiral shape by incorporating a memory shape material, such as Nitinol coil provided, of course, the mechanical properties of the lead body is sufficient so as to allow the body-warmed Nitinol coil to control the shape following removal of the stylet used during the initial installation of the catheter into the right ventricle.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method of fabricating an endocardial defibrillating lead comprising the steps of:
    (a) depositing a conductive electrode on the exterior surface of an elongated flexible, plastic tube;
    (b) advancing said plastic tube over a rigid mandrel having a helical shape;
    (c) heating said plastic tube and mandrel to the softening point of said plastic;
    (d) allowing said tube and mandrel to cool;
    (e) stripping said tube free of said mandrel;
    (f) affixing a conductive tip electrode to the distal end of said tube; and
    (g) electrically joining said conductive electrode and said tip electrode to terminal means at the proximal end of said tube.

2. The method as in claim 1 wherein said plastic is polyurethane.

3. The method as in claim 1 wherein said plastic is silicone rubber.

4. The method as in claim 1 wherein said conductive electrode is electrodeposited onto said tube.

5. The method as in claim 1 wherein said conductive electrode is vapor deposited onto said tube.

* * * * *